United States Patent [19]
Egami

[11] Patent Number: 5,955,669
[45] Date of Patent: Sep. 21, 1999

[54] METHOD AND APPARATUS FOR ACOUSTIC WAVE MEASUREMENT

[75] Inventor: Noritaka Egami, Kobe, Japan

[73] Assignee: Mitsubishi Denki Kabushiki Kaisha, Tokyo, Japan

[21] Appl. No.: 08/896,850

[22] Filed: Jul. 18, 1997

[30] Foreign Application Priority Data

Mar. 6, 1997 [JP] Japan .................................... 9-051793

[51] Int. Cl.⁶ .................................................. G01N 29/04
[52] U.S. Cl. .............................................. 73/579; 73/602
[58] Field of Search ........................... 73/579, 594, 597, 73/602, 615, 616, 628, 630

[56] References Cited

U.S. PATENT DOCUMENTS

| | | | |
|---|---|---|---|
| 3,938,072 | 2/1976 | Baird et al. ................................ | 73/579 |
| 4,305,294 | 12/1981 | Vasile et al. ............................... | 73/579 |
| 4,512,194 | 4/1985 | Beuter ....................................... | 73/579 |
| 5,612,495 | 3/1997 | Shimada et al. ........................... | 73/579 |

FOREIGN PATENT DOCUMENTS 63-247608  10/1988  Japan .

Primary Examiner—John E. Chapman
Attorney, Agent, or Firm—Burns, Doane, Swecker & Mathis, LLP

[57] ABSTRACT

An apparatus and a method for acoustic wave measurement according to the present invention are characterized by oscillating a magnetostrictive vibrator with a frequency to emit an acoustic wave to an object to be measured, calculating the amplitude of a signal received by a wave receiver, and repeating the previous steps throughout a range of different frequencies to detect the resonance frequency. The amplitude of the received signal is calculated from values of the signal sampled at an interval of ¼ of one cycle of the emitted frequency. This reduces the time of the measurement of a thickness a presence of flaws, a presence of impurities and minimizes noises during the measurement.

12 Claims, 21 Drawing Sheets

METHOD AND APPARATUS FOR ACOUSTIC WAVE MEASUREMENT

BACKGROUND OF THE INVENTION

The present invention relates to an improvement of an acoustic wave measuring apparatus used for measuring the dimensions of concrete materials and detecting the acoustic velocity.

Methods of measuring with the use of sound waves the thickness of a material or determining the location of flaws inside a material have been known. FIG. 1 is a schematic view of an acoustic wave measuring apparatus for measuring the thickness of a concrete material (or measuring the velocity of sound waves propagated in a concrete material of which dimensions are known) analogous to one disclosed in Japanese Patent Application Laid-open No. 63-247608 (1988). FIG. 2 is a detailed view showing more details of the apparatus of FIG. 1.

As shown in FIGS. 1 and 2, there are a concrete wall $1a$ to be measured in thickness, an ultrasonic generator 2 mounted directly to the surface of the concrete wall $1a$, an acceleration sensor (or a wave receiver) 3 for detecting vibration of the wall, and a main unit 4 for receiving a detection signal from the wave receiver 3 and for producing and transmitting square-wave pulses to the ultrasonic generator 2. Also, shown are a square-wave pulse variable frequency oscillator 5 (referred to an oscillator hereinafter) of which oscillation frequency can be changed by a command signal, an operational amplifier 6, an NPN transistor 7, resistors 8 and 9, a buffer amplifier 10 for amplifying an output of the wave receiver 3, an A/D converter 11 for converting analog signal to digital signal, a microcomputer 12, and a memory 13. The A/D converter 11, the microcomputer 12, and the memory 13 are grouped to form a spectrum analyzer 32.

The microcomputer 12 instructs the oscillator 5 to generate square-wave pulse voltage of a predetermined frequency. The oscillator 5 transmits the square-wave pulse voltage to the ultrasonic generator 2 which in turn produces oscillation at the frequency to vibrate the target $1a$ to be measured. The ultrasonic generator 2, since it is driven by the square-wave pulse, emits an ultrasonic wave including a plurality of harmonics as its fundamental wave. A vibration in the target $1a$ in a given period of time is then measured in time sequence by the wave receiver 3, amplified by the buffer amplifier 10, with A/D converted in sequence by the A/D converter 11, saved in the memory 13, and subjected to Fourier transform for calculating the amplitude (a crest value of oscillation acceleration) of each frequency component in a range from the oscillation frequency to several times the frequency. It is noted that the buffer amplifier 10 is of a wide frequency range type which can correspond to a wide frequency range of harmonics.

Finally, the oscillation acceleration of frequencies is plotted in a graphic diagram as shown in FIG. 3, in which the horizontal axis represents the frequency and the vertical axis represents the oscillation acceleration or the crest value or amplitude. At a plurality of particular frequencies, transmission waves interfere with reflected waves to generate a standing wave. The resonance frequency of the target $1a$ is then expressed by the frequency with the peak of crest value, and the following equation is established.

$$2L = n \cdot v / f \qquad (1)$$

where L is the thickness of the target or wall $1a$, v is the acoustic velocity across the wall $1a$, f is the resonance frequency, and n is a positive integer.

When v is known, L is given. When L is known, v is calculated. An exemplary process for measuring the thickness is now explained assuming that v is known.

It is understood that the frequency of ultrasonic waves are too high to measure sheets of concrete which have a thickness as small as several meters (i.e. n is too large in the equation (1)) because the acoustic velocity across common concrete materials is 4 to 5 km/s. Therefore, the ultrasonic generator 2 shown in FIG. 2 is replaced by a magnetostrictive vibrator which can produce lower frequencies.

FIG. 4 illustrates an arrangement of the magnetostrictive vibrator 22 in which shown are a magnetostrictive material $22a$ and a couple of weights $22b$ and $2c$ for increasing a force of vibration to the wall $1a$. The magnetostrictive material $22a$ is equipped with coils and magnetized and stressed when the coils are energized, thus generating vibration when receiving an alternating current. The magnetostrictive material $22a$ is classified into two types, one which expands when magnetized and the other which contracts when magnetized. Both types of magnetostrictive materials expand or contract in proportion not to the direction but to the amplitude of a current applied. Therefore, it is essential for producing magnetostrictive vibration of the same frequency as that of an applied alternating current to add a direct current to the alternating current in advance.

For this purpose, the magnetostrictive vibrator 22 is provided with such a pulse voltage as shown in FIG. 5A, which is shifted to the positive side of zero and produced by the oscillator 5 as shown in FIG. 2. The frequency of the pulse voltage can be set by the microcomputer 12. The operational amplifier 6, the transistor 7, and the two resistors 8 and 9 constitute a typical voltage/current converter circuit which permits the magnetostrictive material 22 to receive a pulse current shifted to the positive side of zero.

Since the relation between current input and magnetostrictive action of the magnetostrictive material 22 is nonlinear with hysteresis, the output of vibration fluctuates. The vibration output hence includes different harmonics in addition to the fundamental wave due to the generator 22 being driven by pulses. An example of the waveform of the output of the magnetostrictive vibrator 22 which is driven by a train of voltage pulses (with on-time of current 150 $\mu$s and off-time 350 $\mu$s at a frequency of 2 kHz as shown in FIG. 5A) is shown in FIG. 5B. For demonstrating the presence of harmonics in the output of the magnetostrictive vibrator 22, one second of the waveform for 100 kHz is Fourier-transformed and the result is spectrum-analyzed as shown in FIG. 6.

The vibration output of the magnetostrictive vibrator 22 which is driven by the continuous pulse train of voltage exhibits considerable variations in the amplitude depending on the frequencies. The frequency at which the amplitude of vibration is peaked will thus appear dislocated.

An ideal form of the vibration output of the generator for measurement includes all frequencies required for measurement and its amplitude is uniform throughout the frequencies. If some frequencies are scarce, they can hardly be detected. Variations in the amplitude cause the resonance frequency to be misread hence deteriorating the accuracy of measurement.

In addition, in the case of measuring a floor base of concrete, it is assumed that the concrete is laid on the ground or earth, whose acoustic impedance is similar to that of the concrete as compared with air or water resulting in lower reflectivity of sound wave. Also, the thicker the concrete, the less the reflected waves are received. It is not easy to read the peak of amplitude of acceleration in the vibration where the vibration increases over time (hereinafter "vibration acceleration") on a graph with the frequency plotted along the horizontal axis and the vibration acceleration expressed along the vertical axis.

The amplitude of vibration to be transmitted to a floor base is proportional to the amplitude of a measurement including reflected waves. Hence, fluctuation of the vibration output of the generator 22 directly affects the accuracy of the measurement of vibration amplitude and may disturb precise identification of the peak.

Signals of the vibration acceleration received by the wave receiver 3 have been propagated through different routes A, B . . . , as shown in FIG. 1 and are hard to examine to identify the peak frequencies in the graph shown in FIG. 3. If the resonance frequency fails to be accurately detected, measurement of the thickness will not be dependable and accordingly unsuccessful. While the waveform shown in FIG. 3 is clearly plotted for ease of description, an actual measurement waveform contains a number of noises since the buffer amplifier 10 is a wide frequency range type and easily receives noises. The crest value of each frequency component may be calculated at an acceptable level of accuracy through Fourier transformation of a succession of signals with the spectrum analyzer 32. However, for Fourier transformation of the signals sampled at small intervals of e.g. 1 Hz, the sampling of data takes one second in theory. If measurement is made at different frequencies, the sampling time for 100 frequencies will be increased up to 100 seconds.

FIG. 7 illustrates an exemplary duration of time required for detecting 100 different frequencies through sampling at intervals of 1 Hz with Fourier transformation. As shown, the measurement for 100 different frequencies takes 102 seconds. The measurement for one frequency is repeated 100 times from N1 to N100. This will increase the overall time and be low in the efficiency.

In addition to the problem of efficiency, it is common that the magnetostrictive vibrator 2 is held by an operator directly onto the concrete wall 1a. When the measurement takes substantially 100 seconds, however, the manually holding the generator 2 may vary depending on the pressure or location during the process, thus preventing the measurement from being conducted under uniform conditions.

The conventional acoustic wave measuring apparatus and method hence employ a wide frequency range type of the amplifier for processing a reflected wave thus hardly avoiding the adverse effect of noise. It is also extremely difficult to detect the resonance frequency accurately hence making the measurement difficult.

The time required for the measurement is also too long to maintain the conditions of measurement uniform.

BRIEF SUMMARY OF THE INVENTION

The present invention is directed toward overcoming the foregoing problems and its object is to provide an apparatus and a method for measurement which employ a narrow frequency range type of the amplifier to minimize the effect of noise. Another object of the present invention is to provide an apparatus and a method for measurement of which measuring time is decreased to such a short duration as it will produce no variation of the measurement and identify the resonance frequency with accuracy.

A method for acoustic wave measurement according to the present invention is characterized by comprising: a first step of placing a magnetostrictive vibrator and a wave receiver on one surface of an object to be measured; a second step of oscillating the magnetostrictive vibrator with a predetermined frequency to emit an acoustic wave toward the interior of the object; a third step of receiving by the wave receiver the acoustic wave reflected to an interior location of the object and calculating the amplitude of the received wave corresponding to the predetermined frequency; a fourth step of repeating the process of the second and the third steps a plurality of times, where the magnetostrictive vibrator is produces a frequency which different from the predetermined frequency as well as different every time it is produced; a fifth step of identifying the level of frequency corresponds to the maximum of received amplitudes calculated repeatedly at the fourth step; and a sixth step of calculating the distance from the surface to the interior location of the object or the acoustic velocity through the interior of the object on the basis of the frequency identified at the fifth step.

This allows the measurement of crest value of reflected wave to be conducted at each frequency per reception of wave and thus processed with a narrow band type of a receiver to minimize the development of noise.

Also, the third step may include a step of calculating a first and a second crest values of each signal received by the wave receiver at an interval equal to ¼ of one cycle of the predetermined frequency, and a step of determining the amplitude of the received wave corresponding to the predetermined frequency on the basis of the first and the second crest values.

An acoustic wave measurement apparatus according to the present invention comprises: a magnetostrictive vibrator placed on one surface of an object to be measured for emitting an acoustic wave upon oscillation with a predetermined frequency; a sine-wave variable frequency oscillator for oscillating the magnetostrictive vibrator at the predetermined frequency; a wave receiver placed on the surface of the object for receiving a reflected acoustic wave; a variable frequency band-pass filter for extracting a signal of a directed predetermined frequency from the signal received by the wave receiver; a controller for producing a train of different frequencies in a predetermined order, and directing each of the same frequencies of the train to the sine-wave variable frequency oscillator and the variable frequency band-pass filter at predetermined intervals of time in order; a first amplitude detecting means for detecting a first crest value on the basis of the output signal of the variable frequency band-pass filter during the period in which the variable frequency band-pass filter is supplied with one of the frequencies; a second amplitude detecting means for detecting a second crest value on the basis of the output signal of the variable frequency band-pass filter at an interval of ¼ of one cycle of the frequency after the output signal of the variable frequency band-pass filter is received by the first amplitude detecting means; and a calculating means for calculating the amplitude of the received wave corresponding to the frequency on the basis of the first and the second crest values.

This permits narrow range signal detection thus developing a minimum of noise and reduces the duration required for the total measurement in spite of repeating detection for a multiplicity of frequencies.

Another acoustic wave measurement apparatus according to the present invention is characterized by comprises: a magnetostrictive vibrator placed on one surface of an object to be measured for emitting an acoustic wave upon oscillation with a predetermined frequency; a sine-wave variable frequency oscillator for oscillating the magnetostrictive vibrator at the directed predetermined frequency; a wave receiver placed on the surface of the object for receiving a reflected acoustic wave; a variable frequency band-pass filter for extracting a signal of a directed predetermined frequency from the signal received by the wave receiver; a controller for producing a train of different frequencies by a predetermined order, and directing each of the same frequencies of the train in sequence to the sine-wave variable frequency oscillator and the variable frequency band-pass filter at regular intervals of time; a timing signal generating means for generating, the first and the second timing signals at an interval of ¼ of one cycle of a frequency during the period in which the frequency is supplied to both the sine-wave variable frequency oscillator and the variable frequency band-pass filter; an amplitude detecting means for detecting a first crest value on the basis of the output signal of the variable frequency band-pass filter when receiving the first timing signal, as well as for detecting a second crest value on the basis of the output signal of the variable frequency band-pass filter when receiving the second time signal; and a calculating means for calculating the amplitude of the received wave corresponding to the frequency on the basis of the first and the second crest values.

This hence minimizes the time required for the measurement in spite of the measurement repeated for a multiplicity of the frequencies.

The acoustic wave measurement apparatus of the present invention may further comprise a first oscillation correcting amplifier for controlling the amplification of an output signal of the sine-wave frequency variable oscillator in according with the frequency characteristic of the magnetostrictive vibrator.

The first oscillation correcting amplifier may be corrected the output signal of the sine-wave variable frequency oscillator so that the amplitude of the output from the magnetostrictive vibrator generates a constant level throughout the frequencies.

This allows the vibration output to be easily corrected and thus kept uniform among varied frequencies whereby the resonance frequency will be detected at accuracy.

The acoustic wave measurement apparatus may further comprise a second oscillation correcting amplifier for controlling the amplification of an output signal of the wave receiver in accordance with the frequency characteristic of the magnetostrictive vibrator.

The second oscillation correcting amplifier may be corrected the output signal of the wave receiver so that variations of the amplitude of the output from the magnetostrictive vibrator dependent on the frequencies is eased.

This permits a difference of the vibration outputs among varied frequencies to be easily corrected thus ensuring accurate detection of the resonance frequency.

Also, the acoustic wave measurement apparatus may comprise a first oscillation correcting amplifier for controlling the amplification of an output signal of the sine-wave frequency variable oscillator in accordance with the frequency characteristic of the magnetostrictive vibrator, and a second oscillation correcting amplifier for controlling the amplification of an output signal of the wave receiver in accordance with the frequency characteristic of the magnetostrictive vibrator.

This hence allows the vibration output to be easily corrected and kept uniform among varied frequencies at the transmitter side and a difference of the vibration outputs among varied frequencies to be corrected at the receiver, whereby the resonance frequency will be detected with more accuracy.

The above and further objects and features of the prevent invention will more fully be apparent from the following detailed description with accompanying drawings.

DETAILED DESCRIPTION OF THE INVENTION

Preferred embodiments of the present invention will be described referring to the accompanying drawings.

Embodiment 1

Figure 8:
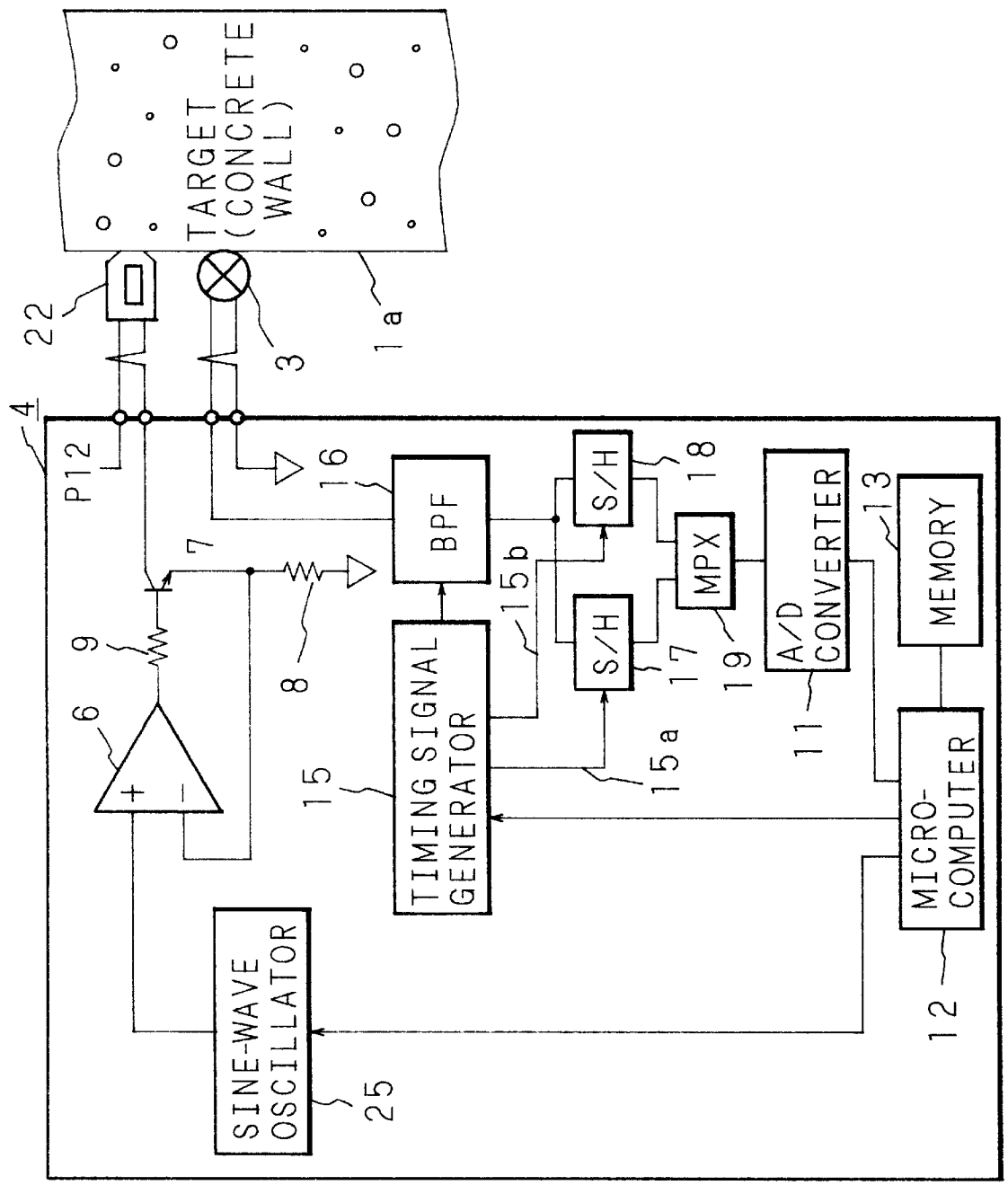
FIG. 8 is a schematic view of an acoustic wave measurement apparatus showing Embodiment 1 of the present invention.

An apparatus and a method for measurement with the use of sound waves according to the present invention are explained in the form of Embodiment 1. Referring to FIG. 8, there are a concrete wall 1a to be measured in thickness, a magnetostrictive vibrator 22 mounted directly on a surface of the concrete wall 1a, an acceleration sensor (wave receiver) 3 for detecting the amplitude of wall vibration, and a main unit 4 of the measuring apparatus for receiving a detection signal from the wave receiver 3 and for producing and transmitting a magnetostrictive drive signal to the magnetostrictive vibrator 22. Also, shown are a sine-wave variable frequency oscillator 25 (referred to a sine-wave oscillator hereinafter) of which oscillation frequency can be changed by a frequency command signal from a microcomputer 12, an operational amplifier 6, an NPN transistor 7, resistors 8 and 9, an A/D converter 11 for converting analog signal to digital signal, the microcomputer 12, and a memory 13.

Also, shown are a timing signal generator 15 responsive to a command from the microcomputer 12 for generating timing signals 15a and 15b used for measurement, a narrow-band variable frequency band-pass filter 16 (referred to a BPF hereinafter) of which band-pass frequency can be changed by a command from the microcomputer 12, a couple of sample/hold circuits 17 and 18, and an analog multiplexer 19.

The action of the apparatus is now explained in which the magnetostrictive vibrator 22 shown in FIG. 8 is driven so that its output includes a minimum of harmonics. For the purpose, the drive is conducted with a sine wave shifted to the positive or negative side of a reference value of zero (wherein equal parts of the sound wave appear above and below said reference value zero, the parts above being in a positive region, the parts below being in a negative region). The use of such shifted sine-wave current permits increasing the fundamental components of frequency while attenuating the harmonics as described previously. In particular, when the characteristic frequency of the magnetostrictive vibrator 22 is fc, an fc component of the output is increased by oscillating the magnetostrictive material at fc/N (N being a positive integer) to promote the effect of intrinsic resonance. However, some harmonics still exist and a signal of vibration acceleration (an amplitude signal) received by the wave receiver 3 includes such harmonics in addition to the fundamental frequency components. Therefore, the BPF 16 is arranged for rejecting the harmonics and passing the fundamental frequency components. It is feasible with the use of a commercially available active filter to remove 99% of the harmonics or reduce the harmonic to apparently zero.

Figure 9:
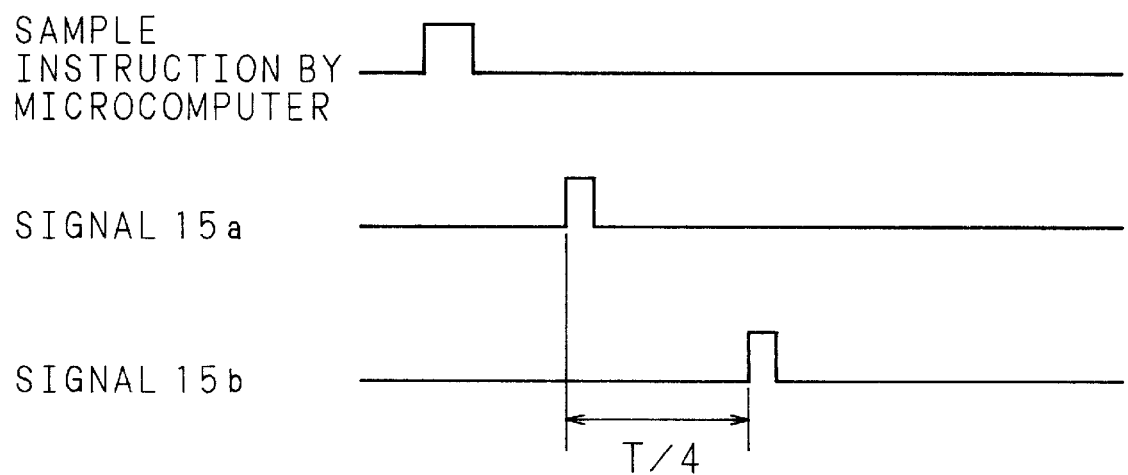
FIG. 9 is an explanatory diagram showing signal outputs of a timing signal generator shown in FIG. 8.

The crest value of the sine wave passed through the BPF 16 is detected by the following manner. In response to a sampling signal from the microcomputer 12, two signal outputs 15a and 16b are released in sequence as shown in FIG. 9. It is predetermined that the difference of timing between the two signal outputs is equal to ¼ of one cycle of the fundamental frequency (corresponding to a phase difference of 90 degrees or 1/(4f) of time difference).

Assuming that the voltage of the fundamental wave is V0sin (wt), the voltage V1 (crest value) sampled by the sample/hold circuit 17 is expressed by:

$$V1 = V0\sin(wt+\alpha).$$

The voltage V2 (crest value) sampled by the sample/hold circuit 18 is expressed by:

$$V2 = V0\sin(wt+\alpha+90°) = V0\cos(wt+\alpha)$$

Hence, the amplitude of received signal V0 is calculated from:

$$V0 = \{(V1)^2 + (V2)^2\}^{1/2} \quad (2)$$

V1 and V2 are then combined by the analog multiplexer 19 in sequence and A/D converted. The crest value is obtained within one cycle of the fundamental wave although the operating time of the BPF 16 is involved. More specifically, when the thickness of the concrete wall 1a is 1 m, the resonance fundamental frequency is about 2 kHz and the calculation of the crest value will be executed within as a short period as 1/2000 seconds. The duration of substantially one second required for measurement of one data (equivalent to N1 in FIG. 7) with a conventional Fourier transform technique is reduced to such a short period as explained above.

Figure 11:
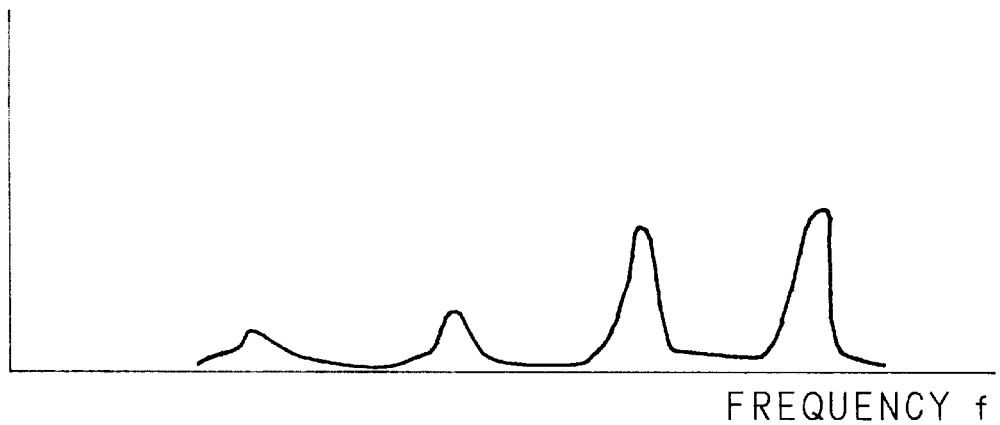
FIG. 11 is an explanatory diagram showing data measured with the apparatus of FIG. 8.

The foregoing procedure of measurement is repeated with the frequency of the sine-wave oscillator 25 and the BPF 16 being changed by a given interval, e.g. 1 Hz, throughout a predetermined frequency range. A resultant waveform of data is shown in FIG. 11. It is understood that the vibration output of the magnetostrictive vibrator 22 becomes unstable just after the change of the frequency and the measurement should be delayed by about 10 times the cycle, as analogous to the conventional method.

Figure 10:
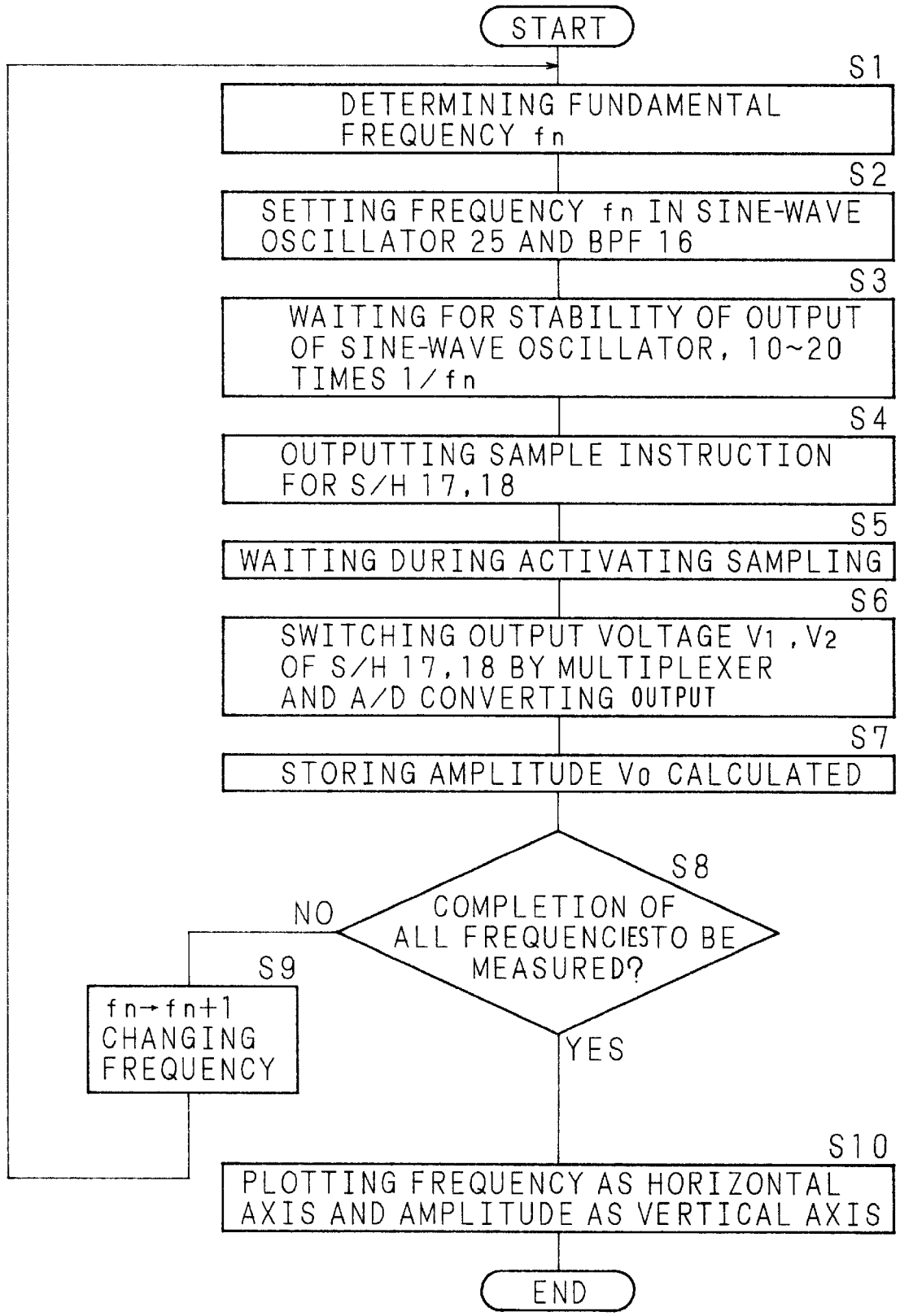
FIG. 10 is a flowchart showing actions of the apparatus of FIG. 8.

FIG. 10 is a flowchart showing the procedure of measurement.

Before starting the procedure of FIG. 10, the magnetostrictive vibrator 22 and the wave receiver 3 are located on the concrete wall 1a to be measured as shown in FIG. 8.

The procedure starts with determining the frequency f1 which stands at (upper or lower) one end of a measuring range of frequencies (fn to fm) (Step S1).

The frequency f1 is applied to the sine-wave oscillator 25 and the BPF 16 for setting (Step S2).

A standby time of about 10 times the cycle is determined which lasts before the output of the sine-wave oscillator 25 is tuned so that it has a stable output (Step S3).

The sample/hold circuits 17 and 18 are set with 1/(4f1) of a time difference (Step S4).

The sample/hold circuits 17 and 18 are actuated for sampling V1 and V2 (Step S5).

V1 and V2 are then fed to the multiplexer 19 (Step S6) and the amplitude V0 corresponding to f1 is calculated (Step S7).

Figure 6:
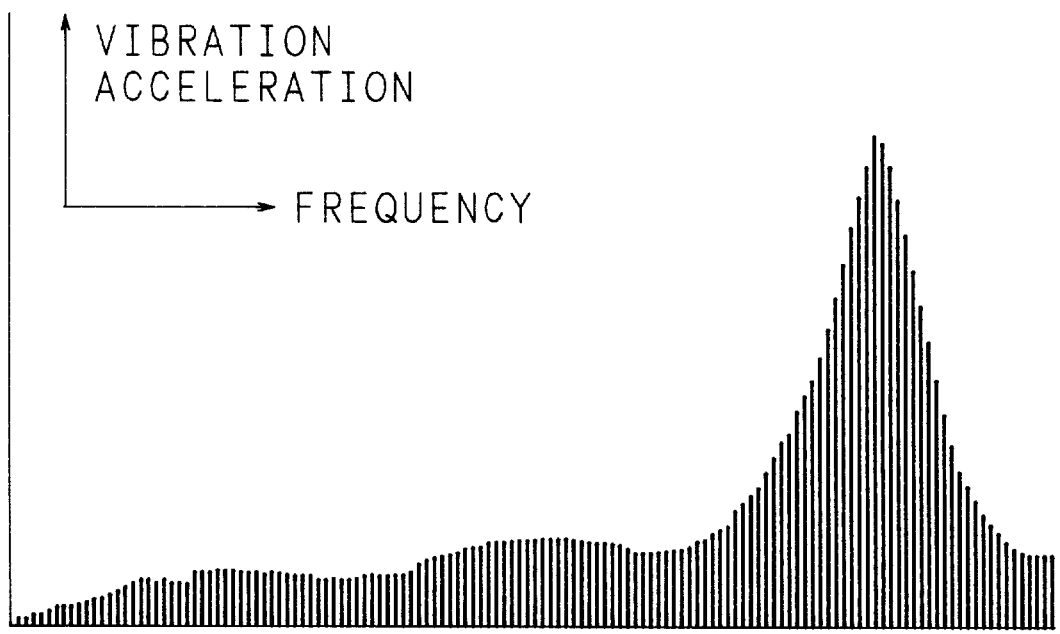
FIG. 6 is a diagram showing an output frequency response of the magnetostrictive vibrator.

This step may be followed by correcting V0 depending on the frequency response of the magnetostrictive vibrator 22 (division with an output of the corresponding frequency shown in FIG. 6).

Although the amplitude V0 at f1 is obtained, the other frequencies (n=2–7) remain not calculated (Step S8).

Before repeating the same steps, the frequency is increased from n to (n+1) by e.g. 1 Hz (Step S9).

The steps S1 to S8 are repeated for the frequency up to f(n+1).

When the full range from fn to fm has been measured, such a resultant waveform as shown in FIG. 11 is given and the resonance frequency is calculated from peak points of the waveform (Step S10).

Finally, the thickness of the concrete wall 1a is computed from the resonance frequency (Step S11) using the equation (1) of the prior art and this step will be explained in no more detail.

The procedure of measurement permits the amplitude of a received signal to be calculated at each fundamental frequency of the output of the vibrator 22. Thus, the frequency pass range of the BPF 16 is minimized and also, the amplitude of the input at each frequency is corrected according to the vibration output, hence lowering the effect of noise and ensuring the accuracy of measurement.

The length of time required for the measurement is now explained. The steps S1 to S3 are identical to those of the conventional method and take e.g. about 1/100 second.

As described, the steps S4 to S8 last as short as 1/2000 seconds per measurement. Therefore, the duration from S1 to S8 is substantially 21/2000 of a second. When the measurement for 100 difference frequencies is conducted and added with the extra step S10 (about one second), the total is:

$$(21/2000) \times 100 + 1 \approx 2 \text{ seconds}$$

Figure 7:
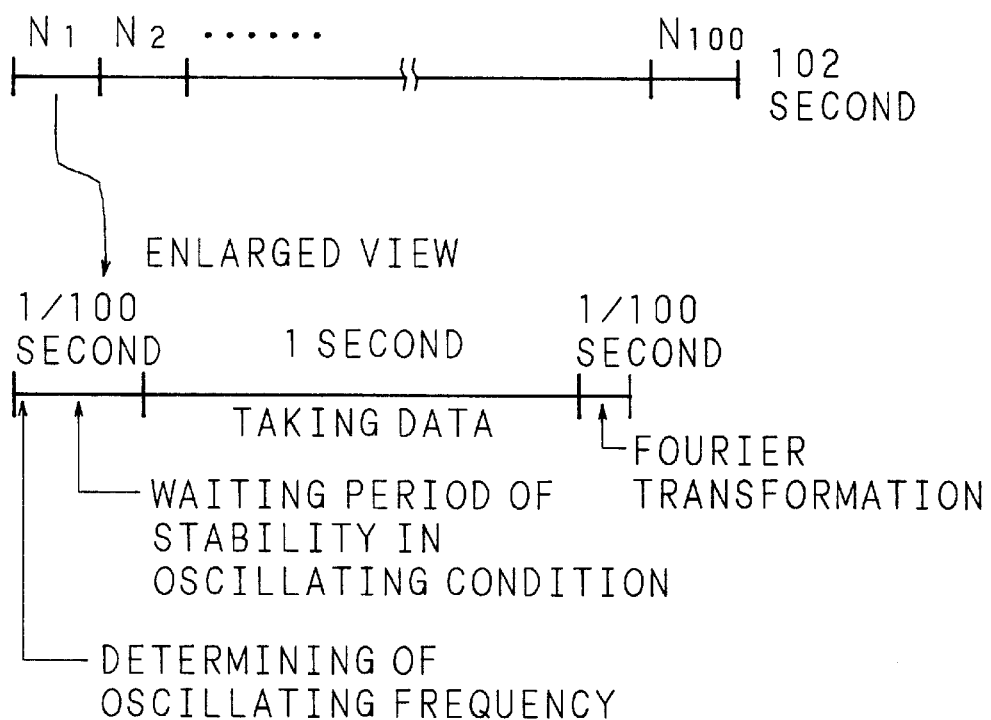
FIG. 7 is an explanatory diagram showing an operating time of the apparatus of FIG. 1.

This duration is much shorter than that shown in FIG. 7.

Figure 12:
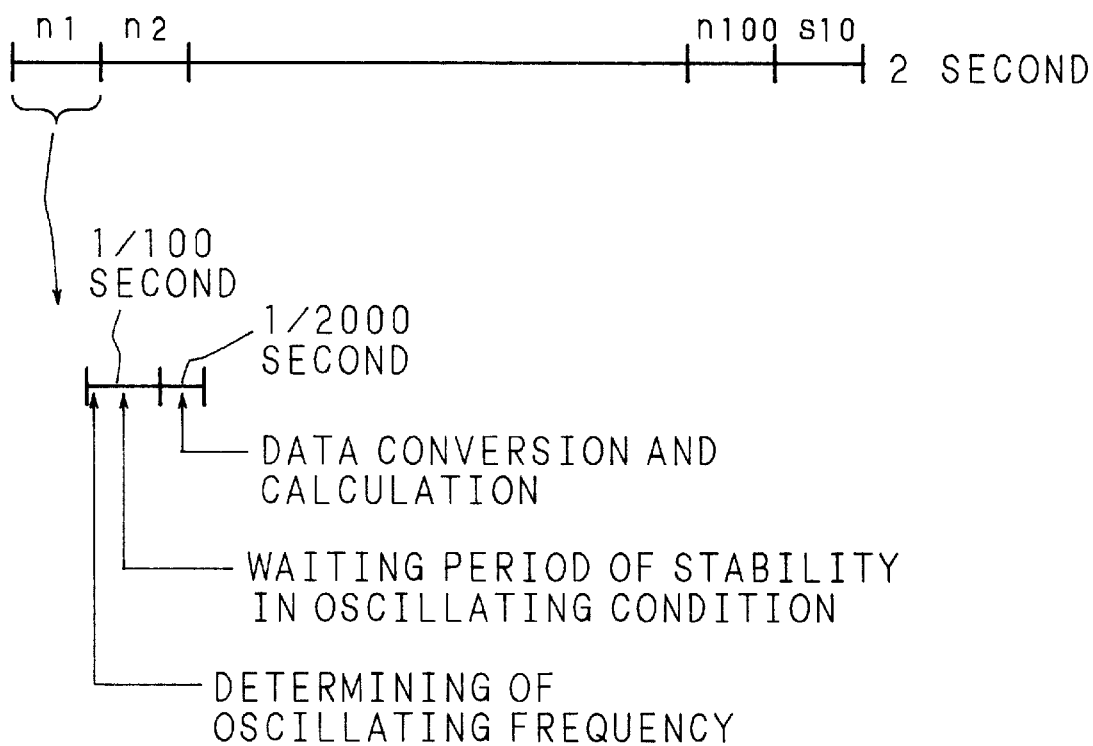
FIG. 12 is an explanatory diagram showing operating time according to the flowchart of FIG. 10.

FIG. 12 illustrates the duration of measurement according to Embodiment 1, in which n1 to n100 indicate 100 times repeating of the procedure from flow steps S1 to S9 shown in FIG. 10.

The timing signal generator 15, the sample/hold circuit 17, and the multiplexer 19 constitute a first amplitude measuring means. Equally, the timing signal generator 15, the sample/hold circuit 18, and the multiplexer 19 constitute a second amplitude measuring means.

The microcomputer 12 and the memory 13 are combined to an operating means for calculating the amplitude of a received wave at the vibration frequency from the equation (2). The operating means also serves as a controller for producing a train of different frequencies and directing each of the same frequencies of the train to the sine-wave oscillator 25 and the variable frequency BPF 16 at predetermined intervals of time in order. Furthermore, the operating means acts as a second operating means for detecting the resonance frequency and calculating the thickness of the concrete wall 1a.

The BPF 16 shown in FIG. 8 may be a lowpass filter of which rejecting frequency range is, for example, about 1.5 times the fundamental frequency. The driving circuit from the amplifier 6 to the transistor 7 is illustrative and of no limitation. Although the target to be measured is a concrete wall in this embodiment, it may be any other materials including metal, plastic, and liquid.

Embodiment 2

Figure 13:
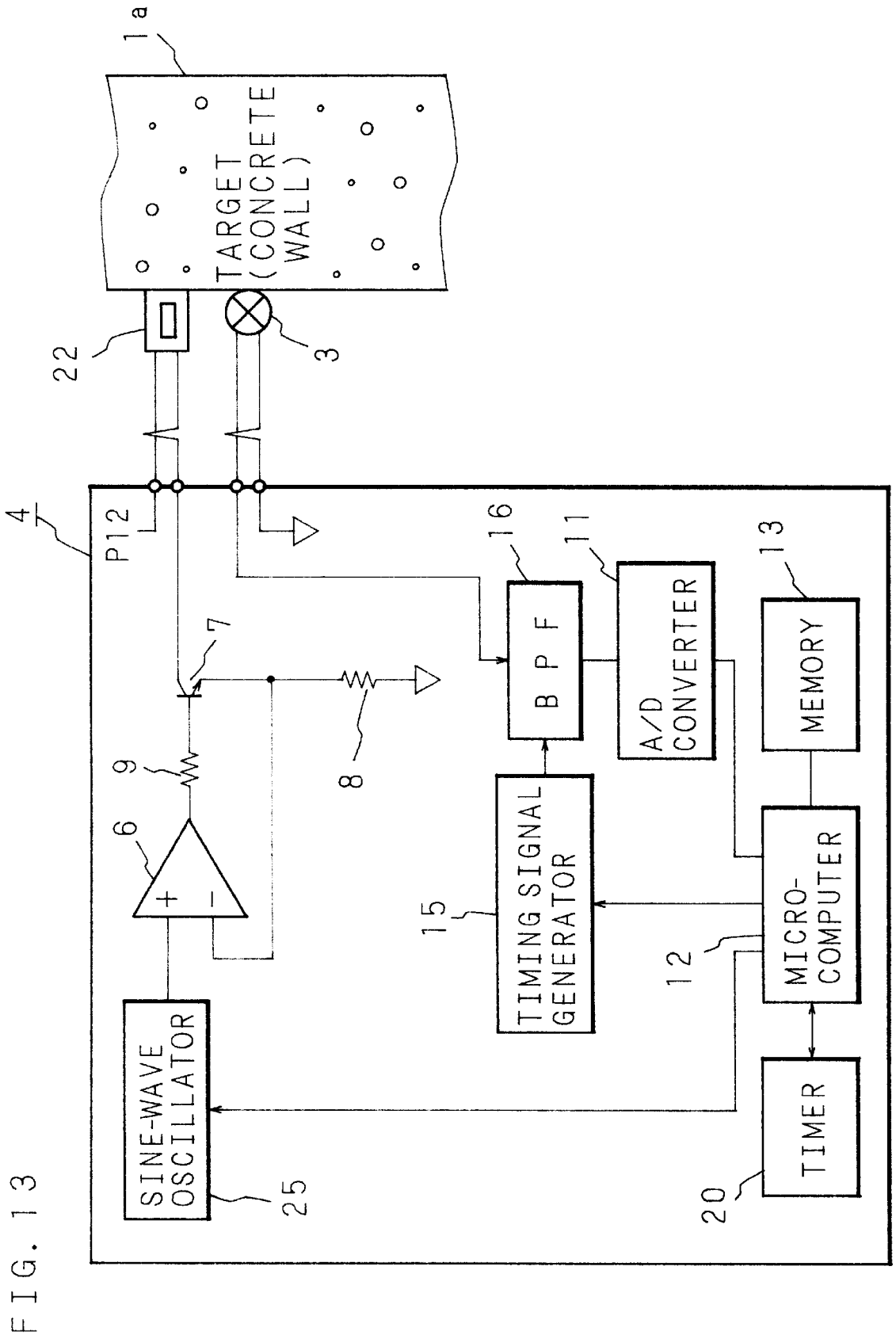
FIG. 13 is a schematic view of an acoustic wave measurement apparatus showing Embodiment 2 of the present invention.
Figure 14:
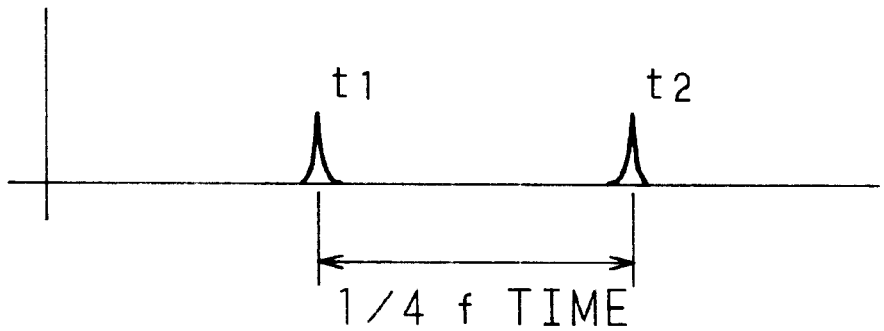
FIG. 14 is an explanatory diagram showing signal outputs of a timer.
Figure 15:
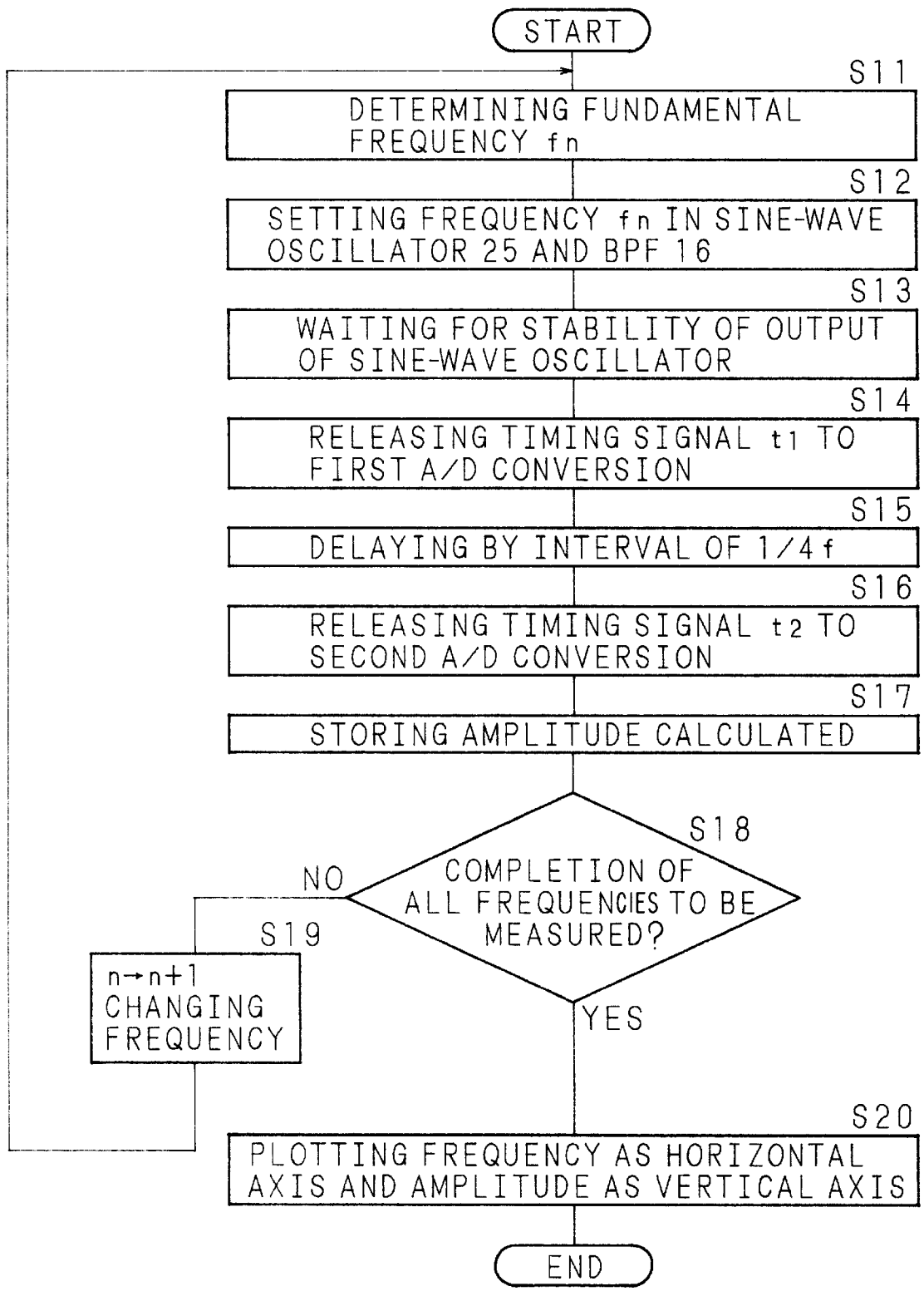
FIG. 15 is a flowchart showing actions of the apparatus of FIG. 13.

FIG. 13 is a schematic view of an acoustic wave measuring apparatus showing Embodiment 2 of the present invention. As shown, denoted by 20 is a timer. Both a sine-wave signal oscillator 25 and a BPF 16 are responsive to a command (indicative of e.g. f) from a microcomputer 12 for determining a setting of the frequency. The BPF 16 has a narrow frequency rejecting range and passes frequencies of the setting range in response to a signal output of a timing signal generator 15. FIG. 14 is an explanatory view showing a signal of the timer 20. A flowchart of measurement in the apparatus shown in FIG. 13 is shown in FIG. 15.

The timer 20 delivers the timing signal two times by an interval of 1/(4f) as shown in FIG. 14. First and second ones of the timing signal are denoted by t1 and t2.

It is assumed that the input which has been A/D converted once in response to releasing of the first timing signal t1 is V1 and the input which has been A/D converted two times in response to releasing of the second timing signal t2 after the interval of 1/(4f) (a delay of 90 degrees) controlled precisely by the timer 20 is V2. The crest value V0 of the fundamental frequency is then calculated from the equation (2) used in Embodiment 1.

It is true that when the frequency is high and 1/(4f) is thus shorter, the sampling time and thus the calculation of measurement in the apparatus shown in FIG. 13 may be declined in accuracy depending on a processing speed of the microcomputer 12. The apparatus shown in FIG. 13 is eligible when the frequency employed is comparatively low.

Although the two signals t1 and t2 spaced by 1/(4f) of the interval are released from the timer 20 in this embodiment, they may be supplied by the timing signal generator 15. It would also be understood that the timer 20 is substituted by a software program operable with the microcomputer 12.

Referring to the flowchart of FIG. 15, the procedure of Embodiment 2 starts with determining the fundamental frequency fn (Step S11). This is followed by setting the sine-wave oscillator 25 and the BPF 16 with f1 (Step S12), giving a standby time before the output of the sine-wave oscillator 25 is turned to be stable (Step S13), releasing the timing signal t1 from the timer 20 to perform a first action of A/D conversion (Step S14), delaying by the interval of 1/(4f) (Step S15), and releasing the timing signal t2 from the timer 20 to perform a second action of A/D conversion (Step S16). Then, the amplitude for f1 is calculated from results of the A/D conversion (Step S17) and it is examined whether or not the remaining of frequencies (n=2–n) are measured (Step S18). If not, n is increased to n+1 and the steps S11 to S18 are repeated (Step S19). When the full range from fn to fm has been measured, measurements are plotted in a graph of the frequency and the crest value and the resonance frequency are calculated from peaks in the graph (Step S20).

Finally, the thickness of a target is computed from the resonance frequency using the equation (1) of the prior art and this step (S21) will be explained in no more detail.

The length of time required for the measurement is explained. The steps S11 to S13 are the same as those shown in FIG. 10 and take e.g. about 1/100 of a second.

The steps S14 to S19 last as short as 2/2000 of a second since the conversion described in Embodiment 1 is repeated two times. Therefore, the duration from S11 to S19 is substantially 22/2000 of a second. When the measurement for 100 difference frequencies is conducted and added with the extra step S20 (about one second), the total is:

$$(22/2000) \times 100 + 1 \approx 2.1 \text{ seconds}$$

This duration is much shorter than that shown in FIG. 7.

Figure 16:
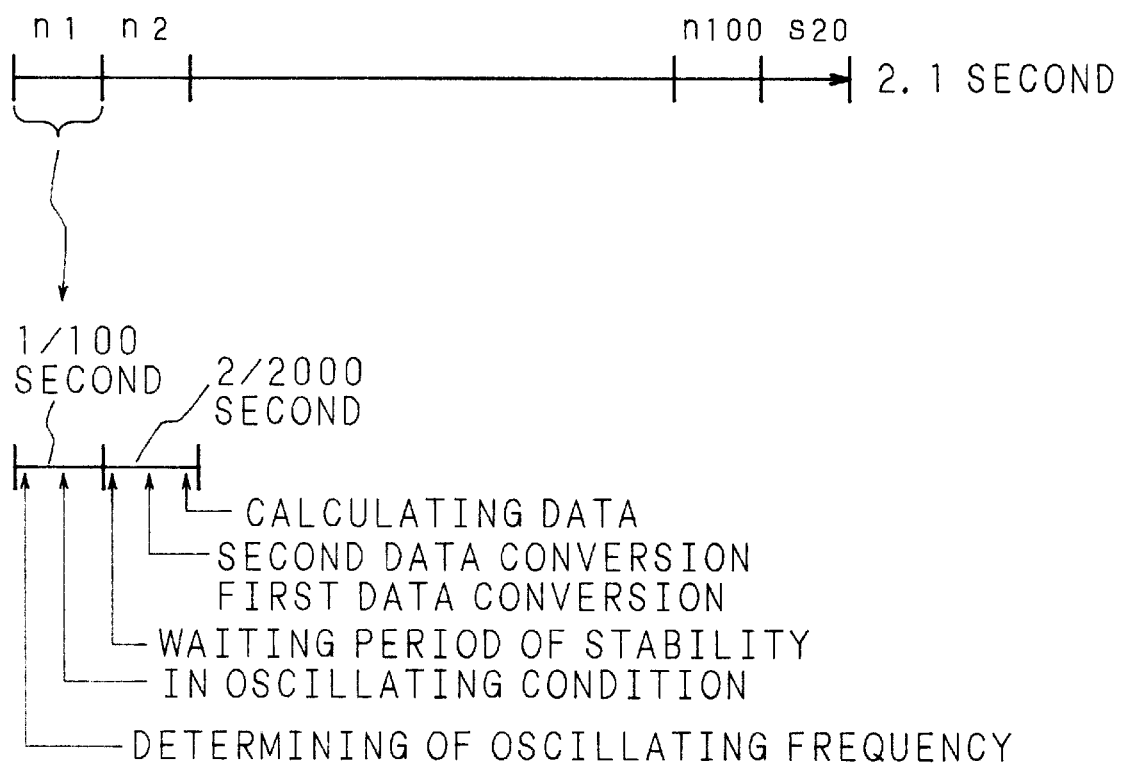
FIG. 16 is an explanatory diagram showing operating time according to the flowchart of FIG. 14.

FIG. 16 illustrates the duration of measurement according to Embodiment 2, in which n1 to n100 indicate 100 times repeating of the procedure from flows S11 to S19 shown in FIG. 15.

The previous embodiments are explained for measuring the thickness of a concrete material when the acoustic velocity through the concrete material is known. It is thus understood that the measurement of the acoustic velocity is equally possible with the thickness being known. Also, the subject to be measured is not limited to the thickness but the presence of flaws or impurities in the concrete or other material may be detected with equal success.

As shown in FIG. 13, a microcomputer 12 and a memory 13 are combined to an operating means for calculating the amplitude of a received wave at the vibration frequency from the equation (2). The operating means also serves as a second operating means for detecting the resonance frequency and calculating the thickness of a concrete wall 1a.

A BPF 16 of FIG. 13 may be a lowpass filter of which rejecting frequency range is, for example, about 1.5 times the fundamental frequency. The driving circuit from an amplifier 6 to a transistor 7 is illustrative and of no limitation.

Embodiment 3

Figure 17:
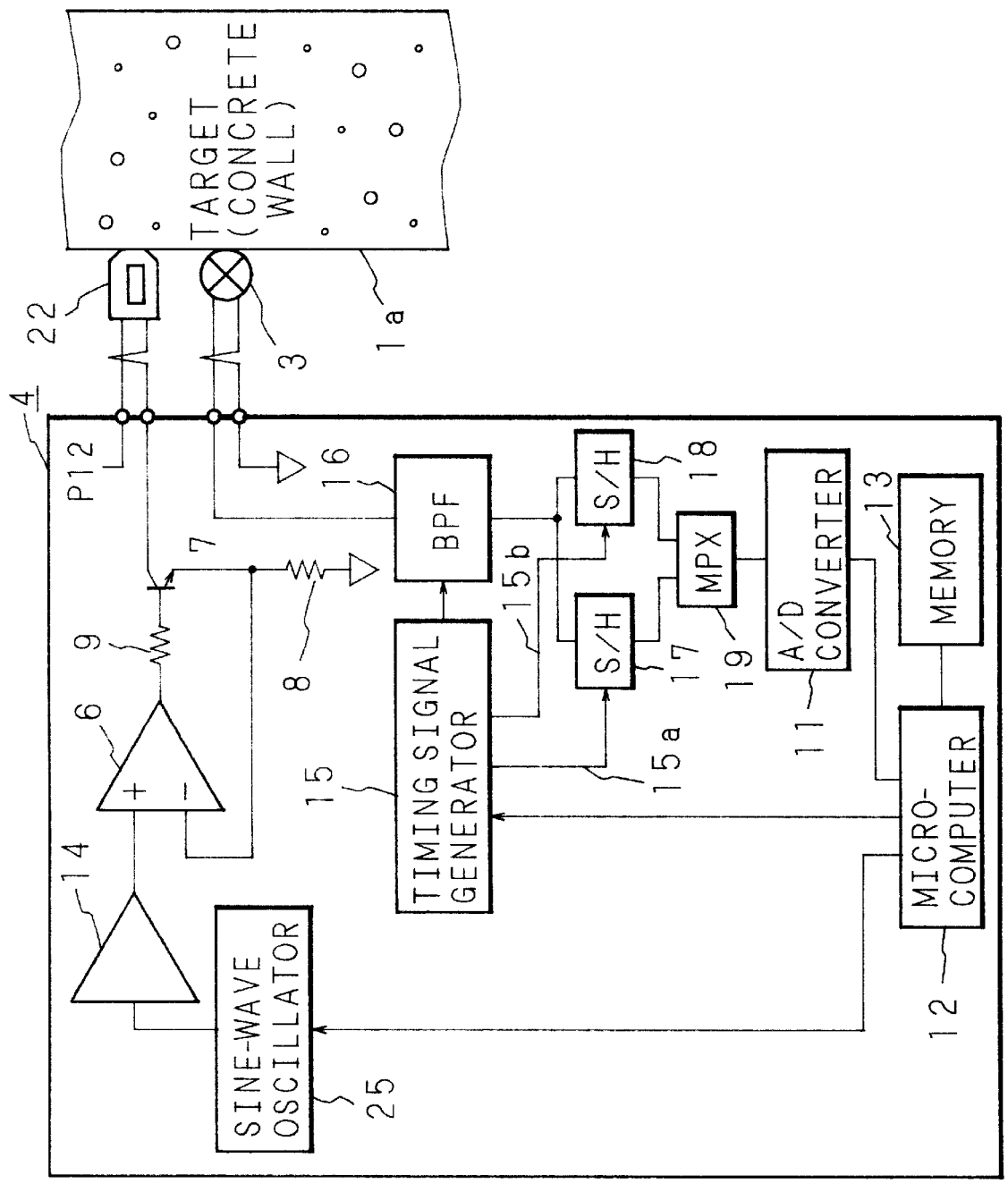
FIG. 17 is a schematic view of an acoustic wave measurement apparatus showing Embodiment 3 of the present invention.

FIG. 17 illustrates an acoustic wave measuring apparatus according to Embodiment 3 of the present invention.

As shown, denoted by 14 is an amplification controllable amplifier (an automatic gain amplifier) of which gain setting can arbitrarily be changed by a microcomputer 12. The other arrangement is identical in both the construction and the function to that shown in FIG. 8. The gain of the automatic gain amplifier 14 is changed corresponding to the frequency response of a magnetostrictive vibrator 22. When the setting frequency is low, the gain is increased to produce a high rate of driving current. When high, the gain is decreased so that the vibration output of the magnetostrictive vibrator 22 is kept uniform regardless of the setting frequency. If all frequencies contained in the vibration output which is generated by conventional pulse drive are used simultaneously, the output for particular frequencies will hardly be controlled. This embodiment employs a fundamental wave and thus allows the output to be adjusted.

For example, the magnetostrictive vibrator 22 is mounted in combination with a wave receiver 3 directly on a concrete structure which has such a thickness that reflected waves are negligible. The amplitude of the fundamental wave detected by the wave receiver 3 is then measured.

Figure 18:
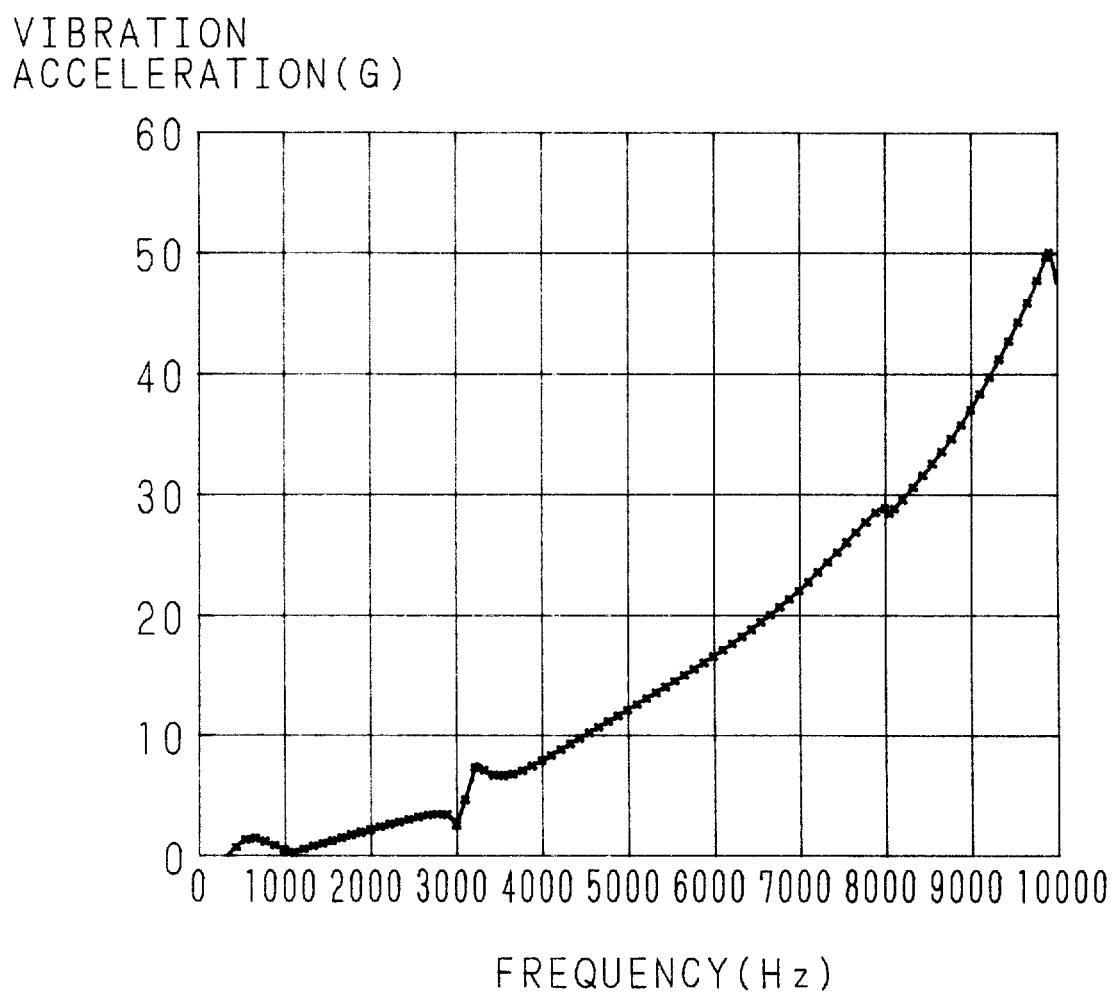
FIG. 18 is a diagram showing a vibration output frequency response of the magnetostrictive vibrator with its drive current maintained uniform.

FIG. 18 shows the relation between the vibration acceleration (of the fundamental wave) and the setting frequency of the magnetostrictive vibrator 22 which is energized with a constant DC bias voltage and a constant sine-wave current. The curve represents measurements as the setting frequency is varied. As apparent, the vibration output is substantially proportional to a square of the frequency but is not completely continuous. Such discontinuous points may represent the effects of non-linear property of a magnetostrictive material and self-resonance derived from dimensional characteristics.

Figure 19:
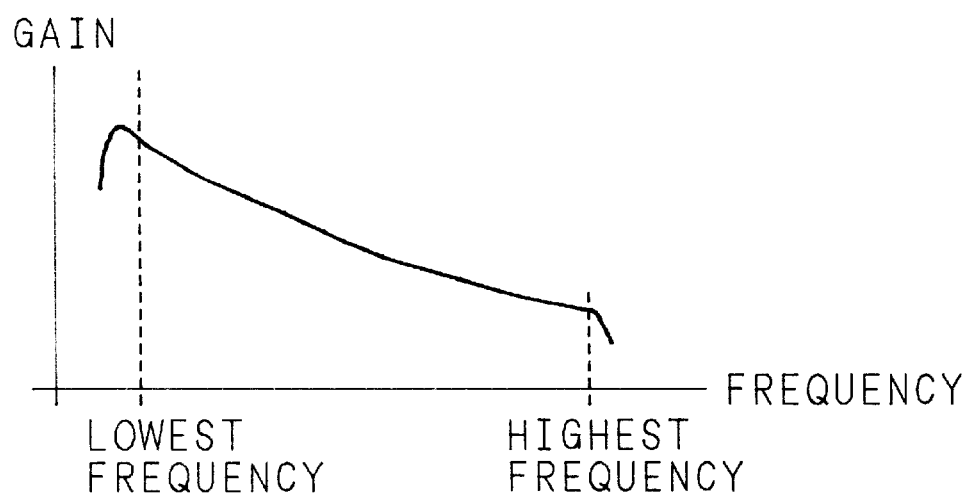
FIG. 19 is a diagram showing a frequency response of an automatic gain amplifier shown in FIG. 17.

The gain (frequency response) of the automatic gain amplifier 14 is so determined that the fundamental waves are uniform in the amplitude throughout the applicable range of vibration frequencies. The frequency response (such as shown in FIG. 19) is saved in a memory 13 and used for setting the gain whenever the vibration frequency is changed.

This allows the vibration output to be uniform throughout the frequencies thus ensuring precise measurement of the frequency peak. It is preferable that the amplification of the automatic gain amplifier 14 is set to a level as low as possible for frequencies above the upper limit and below the lower limit.

Figure 1:
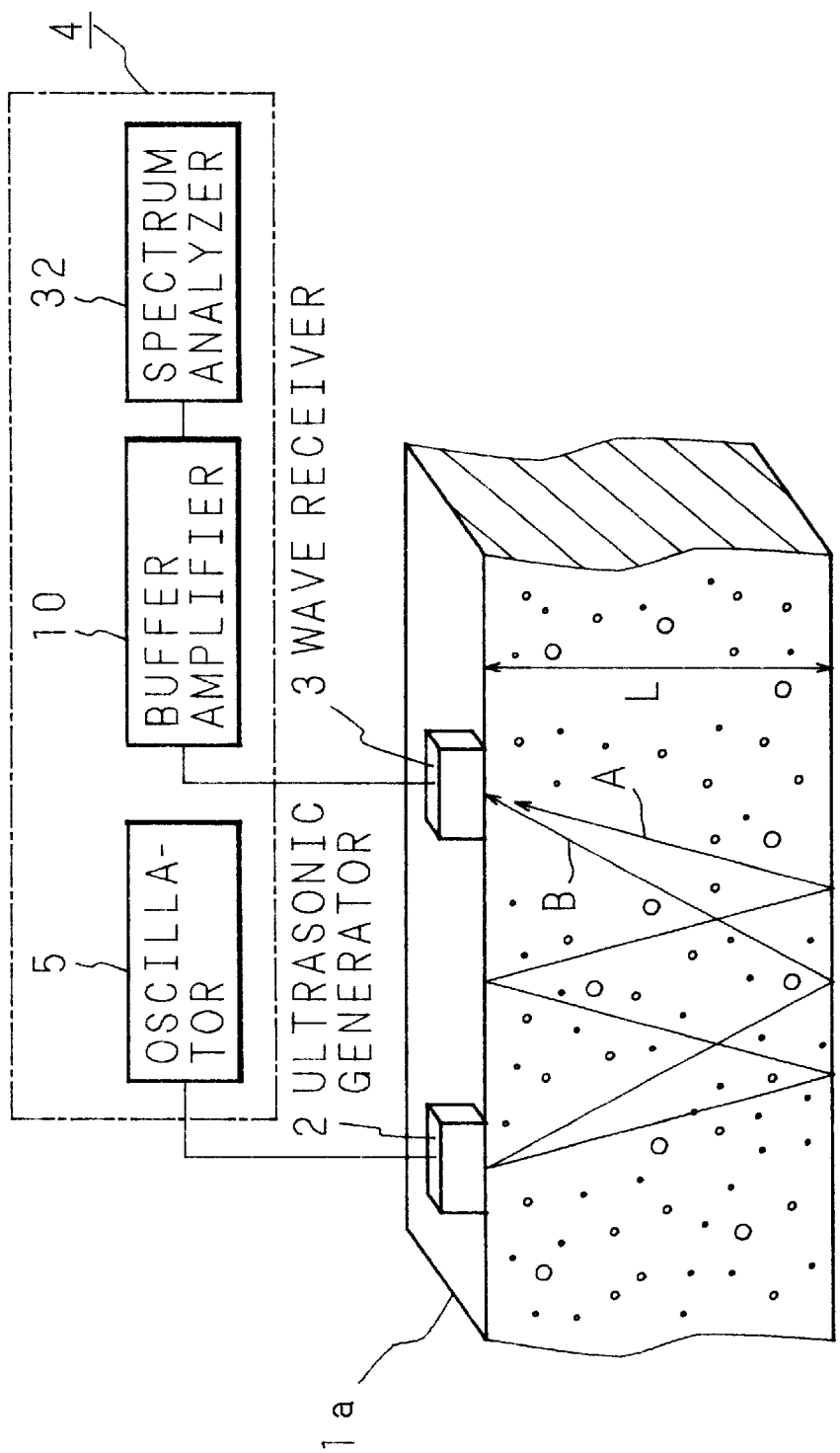
FIG. 1 is a schematic view of a conventional acoustic wave measuring apparatus.
Figure 2:
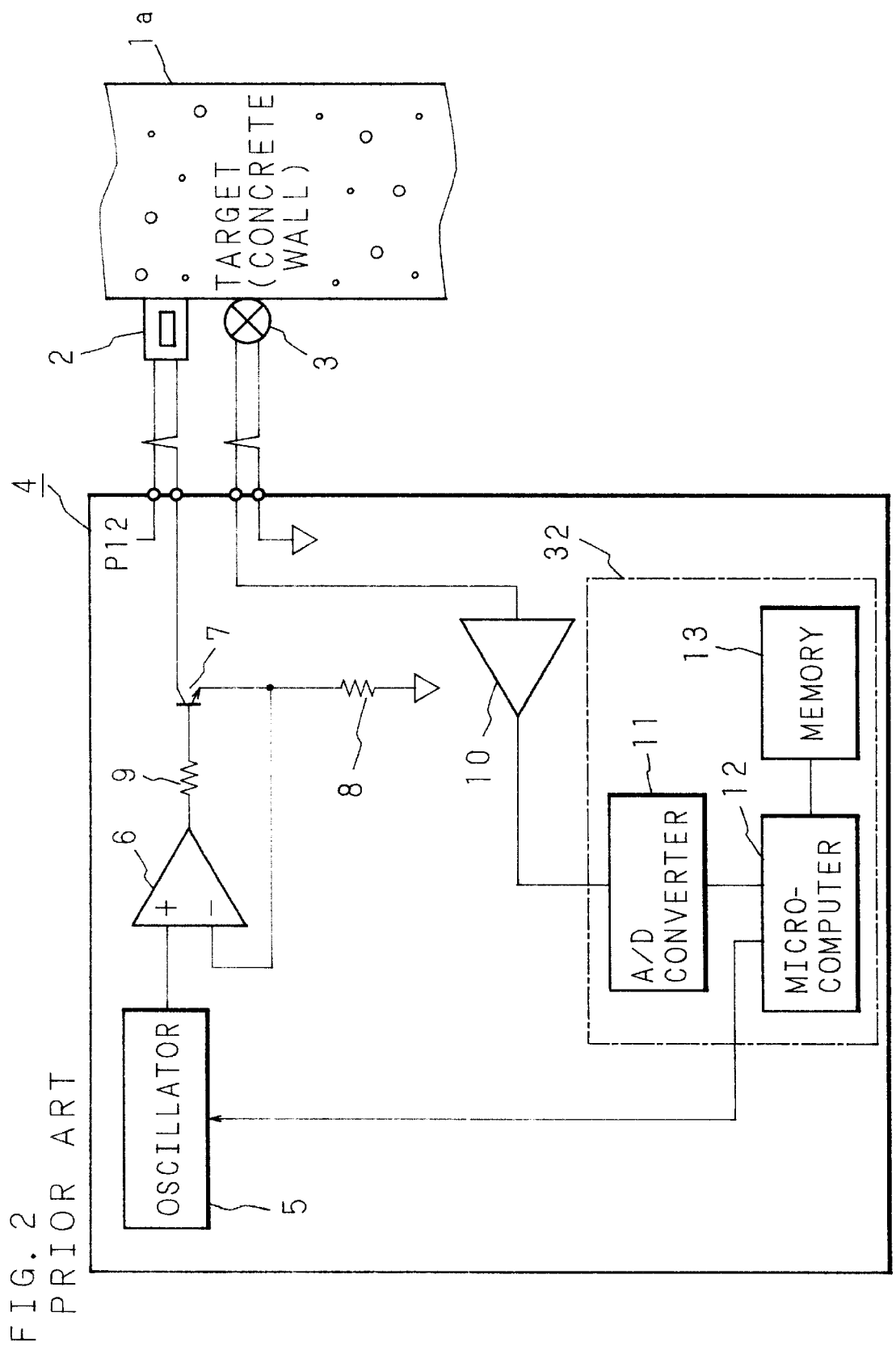
FIG. 2 is schematic detailed view of the apparatus shown in FIG. 1.
Figure 3:
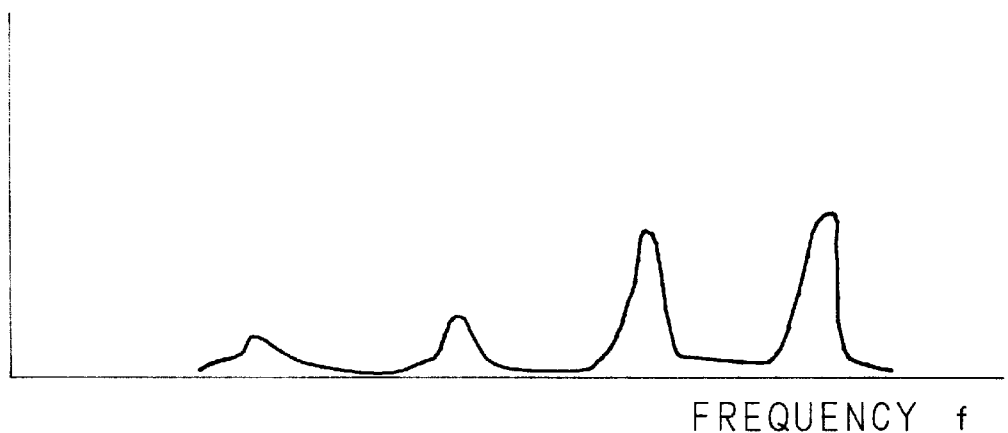
FIG. 3 is an explanatory view showing data measured with the apparatus of FIG. 1.
Figure 4:
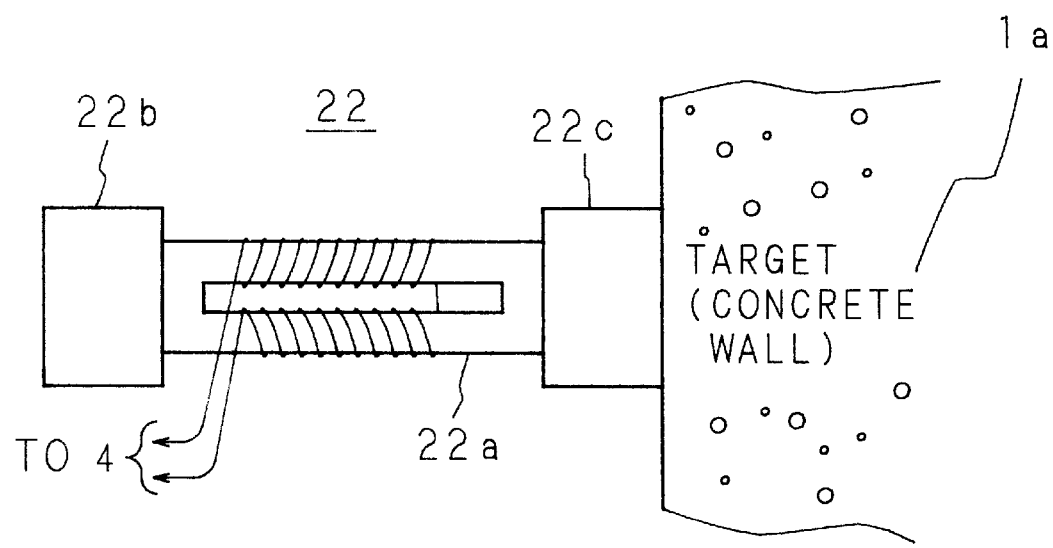
FIG. 4 is an explanatory view showing a construction of a magnetostrictive vibrator.
Figure 5A:
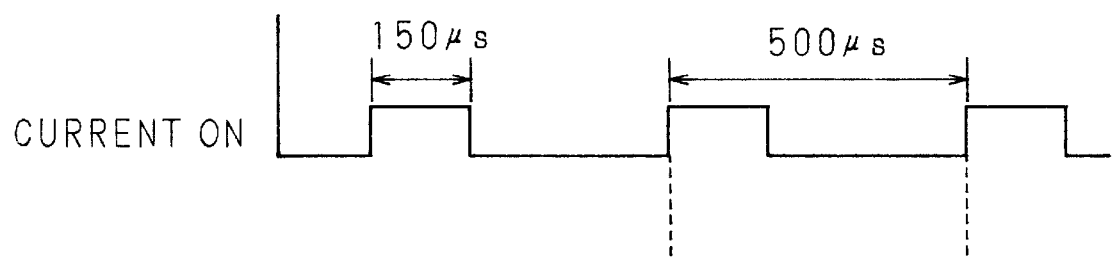
FIGS. 5A and 5B are explanatory diagrams showing an exciting voltage for the magnetostrictive vibrator.
Figure 5B:
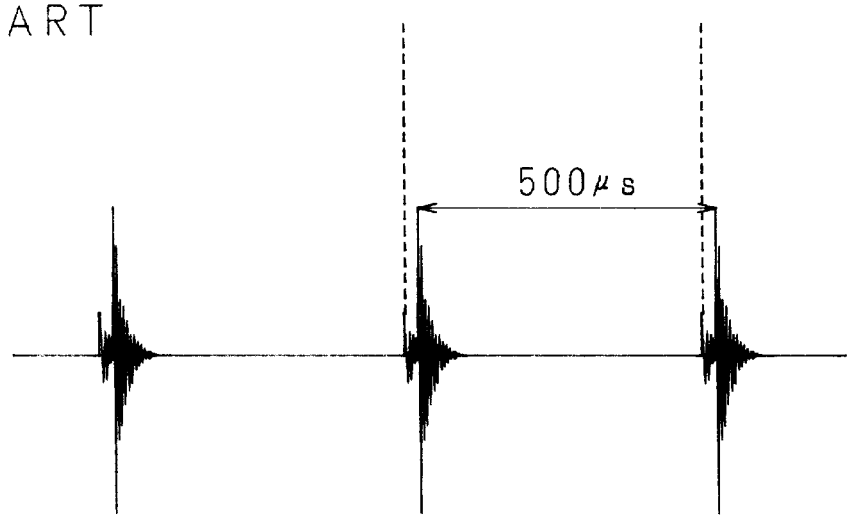

Another technique for measuring the characteristic shown in FIG. 18 may be provided in which the magnetostrictive vibrator 22 is arbitrarily set (e.g. not placed directly on a concrete material but on a floor) and coupled with the wave receiver 3 directly placed on a weight 22c side (FIG. 4) of the vibrator 22. The gain of the automatic gain amplifier 14 is then determined so that the fundamental waves received by the wave receiver 3 are uniform in the amplitude or the crest value when variations of the frequency are used. The automatic gain amplifier 14 is also known as an vibration correcting amplifier.

Although the apparatus described in Embodiment 3 is similar to that of Embodiment 1 shown in FIG. 8, it may be a modification of the apparatus of Embodiment 2 (FIG. 13).

Embodiment 4

Figure 20:
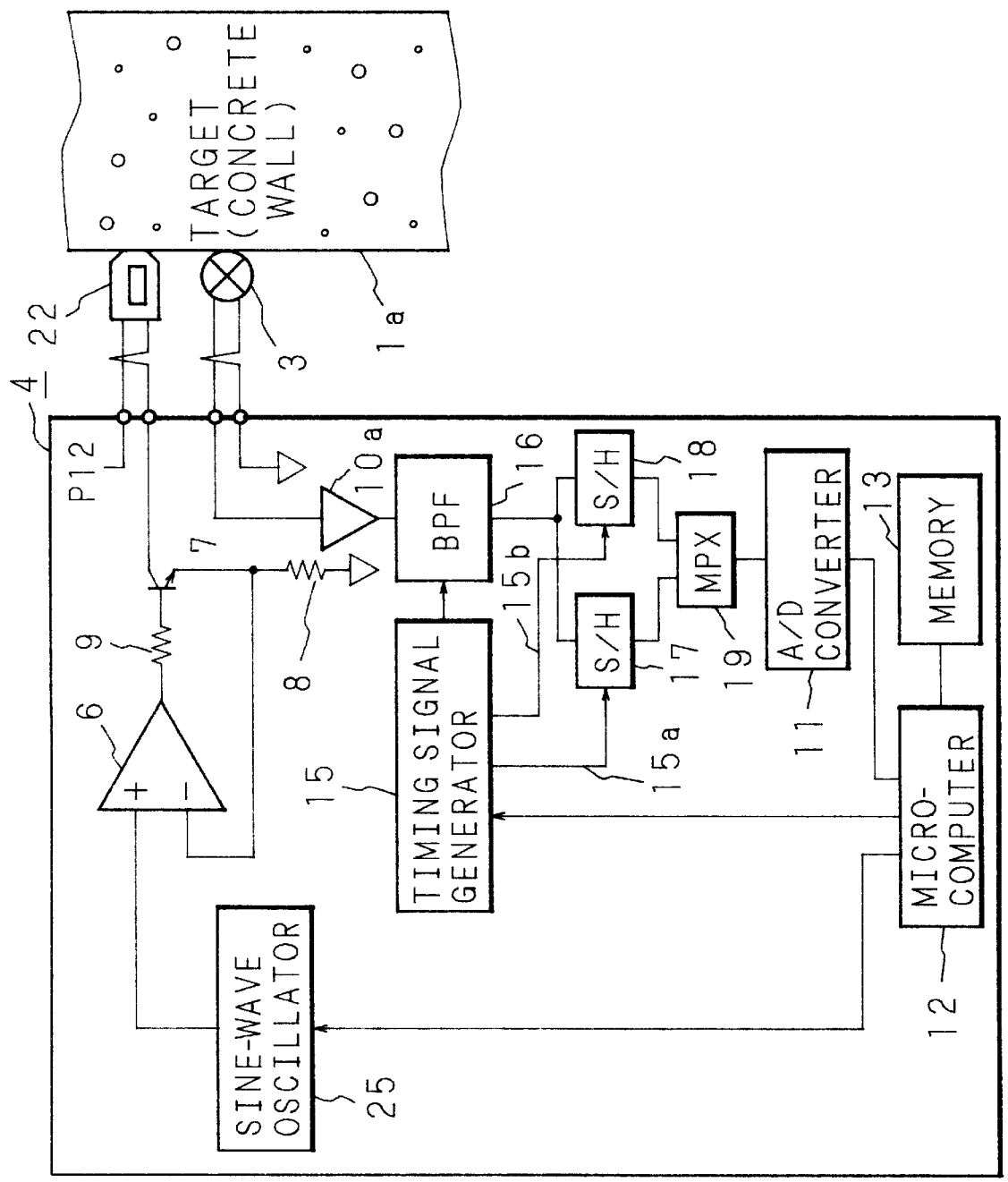
FIG. 20 is a schematic view of an acoustic wave measurement apparatus showing Embodiment 4 of the present invention.

FIG. 20 illustrates an apparatus according to Embodiment 4 of the present invention.

Denoted by 10a is an amplification controllable amplifier (automatic gain amplifier) of which gain can be changed by a microcomputer 12. The other components are identical to those of Embodiment 1 shown in FIG. 8. While a magnetostrictive vibrator 22 is supplied with a constant rate of drive current, the gain of the automatic gain amplifier 10a is increased in response to a low level of the frequency which causes a wave receiver 3 to release a low output. It is decreased when the frequency is high. The automatic gain amplifier 10a is identical in the frequency response to that of Embodiment 3 shown in FIG. 19.

Before starting the measurement, the magnetostrictive vibrator 22 and the wave receiver 3 are mounted on a concrete material of which thickness is high enough to neglect reflected waves and the amplitude characteristic (see FIG. 18) of a fundamental wave received by the wave receiver 3 is examined. The factor (see FIG. 19) for compensating the amplitude characteristic is saved in a memory 13 and used for dividing the crest value of the received amplitude to have a quotient. From the quotient, the frequency of which crest value is peaked is correctly determined without being affected by variations of the output frequency of the magnetostrictive vibrator 22.

If the target is other than such a bulky concrete structure, the wave receiver 3 is coupled directly to the magnetostrictive vibrator 22, as described with Embodiment 3, for detecting the frequency response.

Figure 21:
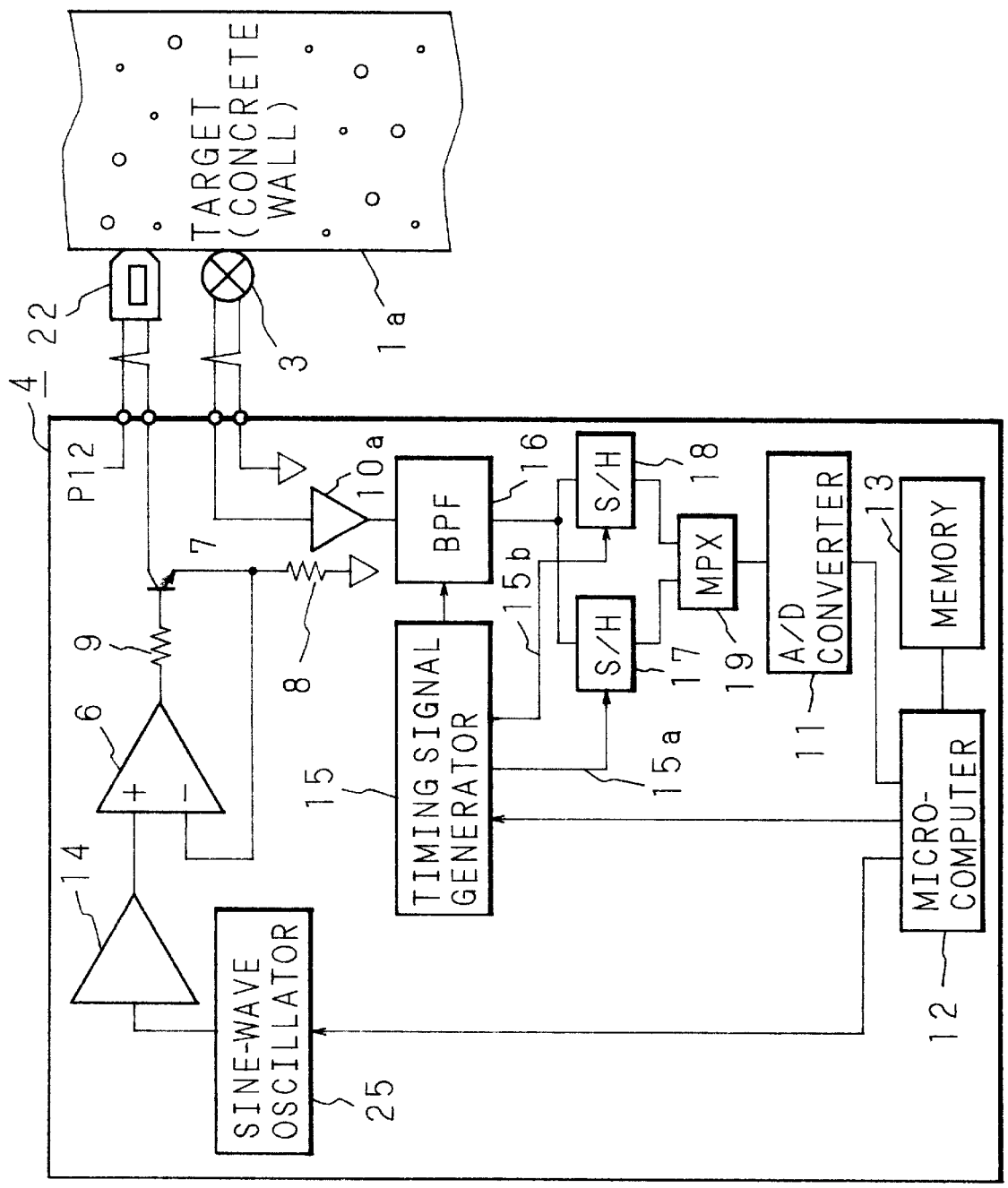
FIG. 21 is a schematic view of an acoustic wave measurement apparatus showing a further embodiment of the present invention.

The gain of the automatic gain amplifier 10a of a common commercially available type consists of eight levels. Hence, the function of the automatic gain amplifier 14 of Embodiment 3 shown in FIG. 17 is hardly eligible in making the vibration output uniform throughout frequencies applied. Also, the automatic gain amplifier 10a shown in FIG. 20 is hardly utilized for handling signal inputs of several millivolts to several bolts due to the presence of noise. The process for amplification is thus shared by both the functions shown in FIGS. 17 and 20. FIG. 21 is a view showing an acoustic wave measuring apparatus equipped with the two automatic gain amplifiers 14 and 10a. The function for determining the gain of the automatic gain amplifier 14 corresponding to the output frequency is identical to that of Embodiment 3 and the other functions are identical to those of Embodiment 4.

The automatic gain amplifier 10a serves as a received wave correction amplifier. The received wave correction amplifier 10a is not necessarily an amplifier but may be a divider for the same function.

As set forth above, the method of acoustic wave measurement according to the present invention comprises the steps of driving the magnetostrictive vibrator with one of frequencies, examining a reflection of the frequency to detect its amplitude, repeating those steps when the frequency has been replaced with another frequency. This allows a narrow band-pass filter to be employed for processing the reflection of the frequency thus ensuring accurate measurement without being affected by pertinent noise. Also, an acoustic wave measurement apparatus of the present invention performs calculation of the amplitude of a signal from two different amplitude levels separated from each other by ¼ of one cycle of the signal as compared with Fourier transform in a conventional apparatus, hence reducing the measurement time considerably. This permits its acoustic wave vibrator and sensor to be held on a target to be measured under an appropriate pressure throughout the measurement time and will thus increase both the efficiency and accuracy of the measurement.

In addition, the magnetostrictive vibrator according to the present invention remains unchanged in the vibration acceleration regardless of variations of the vibration frequency, whereby the peak value of a resonance frequency in the target will be correctly detected as hardly affected by the property of the magnetostrictive vibrator.

Furthermore, the amplitude of a vibration acceleration signal received from magnetostrictive vibrator according to the present invention is corrected in relation to a variation of the frequency output of the magnetostrictive vibrator, whereby the peak of a resonance frequency in the target will correctly be detected.

As the present invention may be embodied in several forms without departing from the spirit of essential characteristics thereof, the foregoing embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

I claim:

1. A method for acoustic wave measurement comprising:
   a first step of placing a magnetostrictive vibrator and a narrow band wave receiver which receives a narrow bandwidth of acoustic waves on one surface of an object to be measured;
   a second step of oscillating the magnetostrictive vibrator with a predetermined frequency to emit an acoustic wave toward the interior of the object;
   a third step of receiving by the narrow band wave receiver the acoustic wave reflected to an interior location of the object and calculating the amplitude of the received wave corresponding to the predetermined frequency;
   a fourth step of repeating the process of the second and the third steps a plurality of times, where the magnetostrictive vibrator produces a frequency which is different from the predetermined frequency as well as different each time it is produced in a sequence of times;
   a fifth step of identifying the frequency corresponding to the maximum of received amplitudes calculated repeatedly at the fourth step; and
   a sixth step of calculating the distance from the surface to the interior location of the object or the acoustic velocity through the interior of the object on the basis of the frequency identified at the fifth step.

2. A method for acoustic wave measurement comprising:
   a first step of placing a magnetostrictive vibrator and a wave receiver on one surface of an object to be measured;
   a second step of oscillating the magnetostrictive vibrator with a predetermined frequency to emit an acoustic wave toward the interior of the object;
   a third step of receiving by the wave receiver the acoustic wave reflected to an interior location of the object and calculating the amplitude of the received wave corresponding to the predetermined frequency, wherein the third step includes a step of calculating a first crest value and a second crest values of each signal received by the wave receiver at an interval equal to ¼ of one cycle of the predetermined frequency, and a step of determining the amplitude of the received wave corresponding to the predetermined frequency on the basis of the first and the second crest values;
   a fourth step of repeating the process of the second and the third steps a plurality of times, where the magnetostrictive vibrator produces a frequency which is different from the predetermined frequency as well as different each time it is produced in a sequence of times;
   a fifth step of identifying the frequency corresponding to the maximum of received amplitudes calculated repeatedly at the fourth step; and
   a sixth step of calculating the distance from the surface to the interior location of the object or the acoustic velocity through the interior of the object on the basis of the frequency identified at the fifth step.

3. An acoustic wave measurement apparatus comprising:
   a magnetostrictive vibrator placed on one surface of an object to be measured for emitting an acoustic wave upon oscillation with a predetermined frequency;
   a sine-wave variable frequency oscillator for oscillating the magnetostrictive vibrator at the predetermined frequency;
   a wave receiver placed on the surface of the object for receiving a reflected acoustic wave;
   a variable frequency band-pass filter for extracting a signal of a directed predetermined frequency from the signal received by the wave receiver;
   a controller for producing a train of different frequencies in a predetermined order, and directing each of the same frequencies of the train to the sine-wave variable frequency oscillator and the variable frequency band-pass filter at predetermined intervals of time in order;
   a first amplitude detecting means for detecting a first crest value on the basis of the output signal of the variable frequency band-pass filter, during the period in which the variable frequency band-pass filter is supplied with one of the frequencies;
   a second amplitude detecting means for detecting a second crest value on the basis of the output signal of the variable frequency band-pass filter at an interval of ¼ of one cycle of the frequency after the output signal of the variable frequency band-pass filter is received by the first amplitude detecting means; and
   a calculating means for calculating the amplitude of the received wave corresponding to the frequency on the basis of the first and the second crest values.

4. The acoustic wave measurement apparatus according to claim 3, further comprising a second calculating means for calculating a resonance frequency from a plurality of frequencies and the corresponding amplitudes of the received wave to determine the distance from the surface to an interior location of the object where the reflection is made or the acoustic velocity through the interior of the object.

5. An acoustic wave measurement apparatus comprising:
   a magnetostrictive vibrator placed on one surface of an object to be measured for emitting an acoustic wave upon oscillation with a predetermined frequency;
   a sine-wave variable frequency oscillator for oscillating the magnetostrictive vibrator at the directed predetermined frequency;
   a wave receiver placed on the surface of the object for receiving a reflected acoustic wave;
   a variable frequency band-pass filter for extracting a signal of a directed predetermined frequency from the signal received by the wave receiver;
   a controller for producing a train of different frequencies by a predetermined order, and directing each of the same frequencies of the train in sequence to the sine-wave variable frequency oscillator and the variable frequency band-pass filter at regular intervals of time;
   a timing signal generating means for generating, a first and a second timing signals at an interval of ¼ of one cycle of a frequency during the period in which the frequency is supplied to both the sine-wave variable frequency oscillator and the variable frequency band-pass filter;

an amplitude detecting means for detecting a first crest value on the basis of the output signal of the variable frequency band-pass filter when receiving the first timing signal as well as for detecting a second crest value on the basis of the output signal of the variable frequency band-pass filter when receiving the second timing signal; and a calculating means for calculating the amplitude of the received wave corresponding to the frequency on the basis of the first and the second crest values.

6. The acoustic wave measurement apparatus according to claim 5, further comprising a second calculating means for calculating a resonance frequency from a plurality of frequencies and the corresponding amplitudes of the received wave to determine the distance from the surface to an interior location of the object where the reflection is made or the acoustic velocity through the interior of the object.

7. The acoustic wave measurement apparatus according to claim 5, further comprising a first oscillation correcting amplifier for controlling the amplification of an output signal of the sine-wave frequency variable oscillator in accordance with the frequency characteristic of the magnetostrictive vibrator.

8. The acoustic wave measurement apparatus according to claim 5, further comprising a second oscillation correcting amplifier for controlling the amplification of an output signal of the wave receiver in accordance with the frequency characteristic of the magnetostrictive vibrator.

9. The acoustic wave measurement apparatus according to claim 5, further comprising:

a first oscillation correcting amplifier for controlling the amplification of an output signal of the sine-wave frequency variable oscillator in accordance with the frequency characteristic of the magnetostrictive vibrator; and a second oscillation correcting amplifier for controlling the amplification of an output signal of the wave receiver in accordance with the frequency characteristic of the magnetostrictive vibrator.

10. The acoustic wave measurement apparatus according to claim 7, wherein the first oscillation correcting amplifier corrects the output signal of the sine-wave variable frequency oscillator so that the amplitude of the output from the magnetostrictive vibrator generates a constant level throughout the frequencies.

11. The acoustic wave measurement apparatus according to claim 8, wherein the second oscillation correcting amplifier is corrected the output signal of the wave receiver so that variations of the amplitude of the output from the magnetostrictive vibrator dependent on the frequencies is eased.

12. The acoustic wave measurement apparatus according to claim 9, wherein the first oscillation correcting amplifier corrects the output signal of the sine-wave variable frequency oscillator so that the amplitude from the output from the magnetostrictive vibrator generates a constant level throughout the frequencies, and the second oscillation correcting amplifier is corrected the output signal of the wave receiver so that variations of the amplitude of the output from the magnetostrictive vibrator dependent on the frequencies is eased.

* * * * *